(12) United States Patent
Thorens

(10) Patent No.: US 12,023,439 B2
(45) Date of Patent: Jul. 2, 2024

(54) REFILLABLE AEROSOL-GENERATING ARTICLE

(71) Applicant: Altria Client Services LLC, Richmond, VA (US)

(72) Inventor: Michel Thorens, Moudon (CH)

(73) Assignee: Altria Client Services LLC, Richmond, VA (US)

( * ) Notice: Subject to any disclaimer, the term of this patent is extended or adjusted under 35 U.S.C. 154(b) by 610 days.

(21) Appl. No.: 17/036,458

(22) Filed: Sep. 29, 2020

(65) Prior Publication Data

US 2021/0007397 A1    Jan. 14, 2021

Related U.S. Application Data

(63) Continuation of application No. 15/638,601, filed on Jun. 30, 2017, now Pat. No. 10,820,632, which is a (Continued)

(30) Foreign Application Priority Data

May 31, 2016    (EP) .................................. 16172264

(51) Int. Cl.
*A24F 40/42*        (2020.01)
*A24F 40/10*        (2020.01)
(Continued)

(52) U.S. Cl.
CPC ............ *A61M 15/06* (2013.01); *A24F 40/40* (2020.01); *A24F 40/42* (2020.01); *H05B 1/0244* (2013.01);
(Continued)

(58) Field of Classification Search
None
See application file for complete search history.

(56) References Cited

U.S. PATENT DOCUMENTS 8,267,086 B2    9/2012  Bruna
2012/0325228 A1*  12/2012  Williams ............. A24B 15/167
131/328

(Continued)

FOREIGN PATENT DOCUMENTS

CN    103974637 A    8/2014
CN    104394721 A    3/2015
(Continued)

OTHER PUBLICATIONS

Russian Office Action and Search Report and English translation thereof dated Oct. 16, 2020.
(Continued)

*Primary Examiner* — Katherine A Will
(74) *Attorney, Agent, or Firm* — Harness, Dickey & Pierce P.L.C.

(57) ABSTRACT

A refillable heated aerosol-generating article for use with an electrically-operated aerosol-generating device has an outlet end for insertion into a user's mouth during use, and a distal end upstream from the outlet end. The article includes a refillable liquid retention section and an aerosol-generation section located within a casing. The refillable liquid retention section includes a liquid retention medium, and the aerosol-generation section is located downstream of the refillable liquid retention section. The liquid retention medium has a capacity to absorb up to 35 microliters of liquid. The article is configured such that, during use, air can be drawn through the article from the distal end to the end, passing through the refillable liquid retention section. The article defines an opening or port for allowing the refillable liquid retention section to be charged with liquid.

20 Claims, 3 Drawing Sheets

Related U.S. Application Data continuation of application No. PCT/EP2017/063057, filed on May 30, 2017.

(51) Int. Cl.
  *A24F 40/40* (2020.01)
  *A61M 15/06* (2006.01)
  *H05B 1/02* (2006.01)
  *H05B 3/44* (2006.01)
  *A24F 15/015* (2020.01)

(52) U.S. Cl.
  CPC .............. *H05B 3/44* (2013.01); *A24F 15/015* (2020.01); *A24F 40/10* (2020.01); *A61M 2205/3653* (2013.01); *A61M 2205/8206* (2013.01); *H05B 2203/021* (2013.01); *H05B 2203/022* (2013.01)

(56) References Cited

U.S. PATENT DOCUMENTS

| | | |
|---|---|---|
| 2014/0338686 A1 | 11/2014 | Plojoux et al. |
| 2014/0373856 A1* | 12/2014 | Zuber ................ A24F 47/00 131/328 |
| 2015/0034103 A1 | 2/2015 | Hon |
| 2015/0313283 A1 | 11/2015 | Collett et al. |
| 2015/0359264 A1 | 12/2015 | Fernando et al. |
| 2016/0128384 A1 | 5/2016 | Luciani et al. |
| 2016/0227837 A1 | 8/2016 | Hammel et al. |
| 2016/0332754 A1 | 11/2016 | Brown et al. |
| 2017/0055585 A1 | 3/2017 | Fursa et al. |
| 2017/0086508 A1* | 3/2017 | Mironov ................ A24C 5/01 |
| 2018/0007971 A1 | 1/2018 | Plojoux et al. |
| 2018/0116277 A1 | 5/2018 | Besso |

FOREIGN PATENT DOCUMENTS

| | | |
|---|---|---|
| EP | 2760303 B1 | 5/2015 |
| GB | 2524295 A | 9/2015 |
| JP | 2006-320286 A | 11/2006 |
| JP | 2010520742 A | 6/2010 |
| JP | 2013520982 A | 6/2013 |
| JP | 2015504653 A | 2/2015 |
| KR | 10-2014-0118983 A | 10/2014 |
| RU | 2608289 C2 | 1/2017 |
| WO | WO-2013/083638 A1 | 6/2013 |
| WO | WO-2014/195859 A2 | 12/2014 |
| WO | WO-2015/082651 A1 | 6/2015 |

OTHER PUBLICATIONS

Extended European Search Report for European Application No. 16172264.0 dated Feb. 8, 2017.
International Search Report and Written Opinion dated Oct. 2, 2017 for corresponding International Patent Application No. PCT/EP2017/063057.
International Preliminary Report on Patentability dated Dec. 13, 2018.
Korean Office Action for corresponding Application No. 10-2018-7031663, dated Jan. 27, 2023, English Translation included.
Korean Office Action for corresponding Application No. 10-2018-7031663, dated Jul. 18, 2022, English Translation included.
Chinese Office Action and English translation thereof dated Jan. 6, 2021.
Japanese Decision of Final Rejection for corresponding Application No. 2018-558741, dated Jan. 17, 2022, English translation included herewith.
Chinese Notice of Allowance for corresponding Application No. 201780028196.7, dated Nov. 25, 2021.
Russian Notice of Allowance and English translation thereof dated Jan. 27, 2021.
Japanese Notice of Rejection for corresponding Application No. 2018-558741, dated May 24, 2021.
Korean Notice of Allowance for corresponding Application No. 10-2018-7031663, dated Jul. 20, 2023, English Translation included.

\* cited by examiner

REFILLABLE AEROSOL-GENERATING ARTICLE

CROSS-REFERENCE TO RELATED APPLICATIONS

This application is a continuation of, and claims priority under 35 U.S.C. § 120 to, U.S. application Ser. No. 15/638,601, filed Jun. 30, 2017, which is a continuation application of PCT Application No. PCT/EP2017/063057 filed on May 30, 2017, which claims priority to European Patent Application No. 16172264.0 filed on May 31, 2016, the entire contents of each of which are incorporated herein by reference in their entirety.

BACKGROUND

1. Field

Example embodiments relate to a refillable aerosol-generating article for use with an aerosol-generating device and to an aerosol-generating system. The refillable aerosol-generating article may include a refillable liquid retention medium.

2. Description of the Related Art

Recent years have seen the emergence of two main categories of heated aerosol-generating systems that produce an inhalable aerosol by heating rather than by burning an aerosol-forming substrate. One system, which may be described as an electronic-vapor (e-vapor) system, typically includes a liquid aerosol-forming substrate contained within a cartridge of an atomiser unit. During operation, liquid is conveyed from the cartridge via a wick and is vaporized via a heating coil. A second system, which may be described as a heated tobacco system, involves the heating of a solid substrate including modified tobacco to produce an inhalable aerosol.

SUMMARY

One disadvantage of the e-vapor system is that direct heating of the liquid substrate with a heating coil risks overheating of the liquid, particularly when the cartridge is near to empty.

A heated tobacco system using a consumable article containing a solid aerosol-forming substrate may produce a sensorially more acceptable aerosol and does not present the same hygiene challenges that may be associated with e-vapor systems. However, a user may desire the wider variety of flavors that are possible with a liquid-based heated e-vapor system.

Example embodiments relate to a refillable heated aerosol-generating article for use with an electrically-operated aerosol-generating device, the refillable aerosol-generating article having an outlet end and a distal end upstream from the outlet end, the refillable heated aerosol-generating article including a refillable liquid retention section within a casing and an aerosol-generation section within a casing, the refillable liquid retention section including a liquid retention medium having a capacity to absorb up to 35 microliters of liquid, and the aerosol-generation section being located downstream of the refillable liquid retention section, wherein the refillable heated aerosol-generating article is configured such that air can be drawn therethrough from the distal end to the outlet end, passing through the refillable liquid retention section, and the refillable heated aerosol-generating article defines an opening or port for allowing the refillable liquid retention section to be filled with liquid.

Example embodiments further relate to an aerosol-generating kit including a refillable heated aerosol-generating article for use with an electrically-operated aerosol-generating device, the refillable aerosol-generating article having an outlet end and a distal end upstream from the outlet end, the refillable heated aerosol-generating article including a refillable liquid retention section within a casing, and an aerosol-generation section within a casing, the refillable liquid retention section including a liquid retention medium having a capacity to absorb up to 35 microliters of liquid, and the aerosol-generation section being located downstream of the refillable liquid retention section, wherein the refillable heated aerosol-generating article is configured such that air can be drawn therethrough from the distal end to the outlet end, passing through the refillable liquid retention section, and the refillable heated aerosol-generating article defines an opening or port for allowing the refillable liquid retention section to be filled with liquid, and a dispenser of aerosol-forming liquid, the dispenser being configured to dispense a metered dose of the aerosol-forming liquid through the opening or port of the refillable heated aerosol-generating article to charge the liquid retention section.

Example embodiments also relate to an aerosol-generating system including a refillable heated aerosol-generating article for use with an electrically-operated aerosol-generating device, the refillable aerosol-generating article having an outlet end and a distal end upstream from the outlet end, the refillable heated aerosol-generating article including a refillable liquid retention section within a casing, and an aerosol-generation section within a casing, the refillable liquid retention section including a liquid retention medium having a capacity to absorb up to 35 microliters of liquid, and the aerosol-generation section being located downstream of the refillable liquid retention section, wherein the refillable heated aerosol-generating article is configured such that air can be drawn therethrough from the distal end to the outlet end, passing through the refillable liquid retention section, and the refillable heated aerosol-generating article defines an opening or port for allowing the refillable liquid retention section to be filled with liquid, and an electrically-operated aerosol-generating device, wherein the refillable heated aerosol-generating article is configured to engage with the electrically-operated aerosol generating device, and the electrically-operated aerosol-generating device is configured to supply energy to volatilise liquid retained in the liquid retention section.

BRIEF DESCRIPTION OF THE DRAWINGS

The example embodiments are further described, by way of example only, with reference to the accompanying drawings in which.

DETAILED DESCRIPTION

An aerosol-generating article for use with an aerosol-generating device may be provided. The aerosol-generating article, which is a heated aerosol-generating article, may be referred to herein as the "article." The article may be configured to be suitable for use with an electrically-operated aerosol-generating device. The refillable aerosol-generating article has an outlet end configured to be inserted into a user's mouth during use, and a distal end upstream from the outlet end. The article may also include a refillable liquid retention section and an aerosol-generation section located within a casing. The refillable liquid retention section may include a liquid retention medium, which may be configured to absorb up to 35 microliters of liquid, and the aerosol-generation section is located downstream of the refillable liquid retention section. The article is configured such that, during use, air can be drawn through the article passing through, or over, the refillable liquid retention section. In some example embodiments, air is drawn through the article from the distal end to the outlet end. The article defines an opening or port for allowing the refillable liquid retention section to be charged with liquid.

In some example embodiments, the opening or port may be defined through the distal end of the article. Alternatively, the opening or port may be defined through the casing at a point between the distal end and the outlet end. A port for filling the re-fillable aerosol-generating device may have a closure, for example an openable closure or a valve.

The refillable aerosol-generating article provides a user with the opportunity to prime the article with a liquid aerosol-forming substrate prior to use, for example immediately prior to use. For example, a dose of liquid aerosol-forming substrate may be injected into the liquid retention medium prior to use, for example immediately prior to use.

In one example embodiment, the liquid retention medium has a capacity to absorb up to 35 microliters of liquid. The expression 'up to 35 microliters of liquid in this context means that the liquid retention medium has a capacity to absorb 35 microliters of liquid or less. The liquid retention medium may thus be configured to absorb e.g. 2-35 microliters of liquid, or 5-35 microliters of liquid.

In an example embodiment, the liquid retention medium may be configured to absorb 0-35 microliters of liquid, which may correspond to up to 20 puffs. In an example embodiment, the liquid retention medium may be configured to absorb 15-35 microliters of liquid. In an example embodiment, the liquid retention medium may be configured to absorb 25-35 microliters of liquid or 30-35 microliters of liquid, which may correspond to between 12 and 17 puffs, or between 15 and 17 puffs, respectively.

In one example embodiment, the liquid retention medium may be configured to absorb about 35 microliters of liquid. In one example embodiment, the liquid retention medium may be configured to absorb up to 30 microliters of liquid. In one example embodiment, the liquid retention medium may be configured to absorb up to about 27 microliters of liquid.

In one example embodiment, the liquid retention medium does not have any additional capacity. In an example embodiment, the article includes the liquid retention medium, which has a capacity to absorb up to 35 microliters of liquid, but includes neither any additional liquid retention medium nor any other liquid container. Therefore, the liquid retention article may only contain the liquid aerosol-forming substrate in an amount sufficient for a single use. In such embodiment, the article has to be refilled before every use. In an example embodiment, the liquid retention medium has a capacity to absorb up to 30 microliters of liquid. In an example embodiment, the liquid retention medium has a capacity to absorb 5-30 microliters of liquid, which may correspond to between 3 and 15 puffs. In an example embodiment, the liquid retention medium has a capacity to absorb 20-30 microliters of liquid, which may correspond to between 10 and 15 puffs. In an example embodiment, the liquid retention medium has a capacity to absorb up to 25 microliters of liquid, which may correspond to up to 13 puffs. In an example embodiment, the liquid retention medium has a capacity to absorb up to 20 microliters of liquid. In an example embodiment, the liquid retention medium has a capacity to absorb up to 15 microliters of liquid.

The liquid aerosol-forming substrate may be kept in a hygienic container until the moment of delivery to the article. A user has the opportunity to load a different liquid aerosol-forming substrate for each use.

The refillable aerosol-generating article is a re-usable article that may be consumed by coupling or engaging with an aerosol-generating device, for example an electrically-operated aerosol-generating device. The article is removably couplable with the aerosol-generating device. A method of using the refillable aerosol-generating article may include the steps of providing a dose of liquid aerosol-forming substrate to the liquid retention medium, coupling the article to an aerosol-generating device, activating a heating means, or heater, of the aerosol-generating device, and drawing air through the heated aerosol-generating article. Liquid aerosol-forming substrate retained within the aerosol-generating article is then vaporized by heat energy supplied by the heating means, or heater, and condenses to form an aerosol entrained in the air. When the use is over, for example when the aerosol-forming substrate has been consumed, the article may be removed from the device.

In some example embodiments, the heating means, or heater, heats air that is drawn into the heated aerosol-generating device, the heated air passing over or through the liquid retention medium of the article to vaporize the liquid aerosol-forming substrate and allow formation of an aerosol. Alternatively, air may be heated to a temperature of about 200° C. to 220° C. before passing over or through the liquid retention medium. In some example embodiments, the air with entrained volatile components subsequently cools to a temperature of about 100° C. within the article, allowing the volatile components to condense and form an aerosol. The heater or heating means may alternatively heat the liquid retention medium by conduction or radiation in order to vaporize the liquid aerosol-forming substrate and allow formation of an aerosol.

The liquid aerosol-forming substrate does not directly contact a heating element and, thus, challenges with overheating of the aerosol-forming substrate do not occur.

Articles may be filled with a wide range of different liquid aerosol-forming substrate compositions, thereby providing the user with the wide range of flavors and experiences that can be provided by e-vapor systems. In example embodiments, the articles may be consumed using aerosol-generating devices configured for heating aerosol-generating articles including solid aerosol-forming substrates. Thus, a user may select either a tobacco containing heated aerosol-generating article or select a refillable article and fill it with a liquid aerosol-forming substrate, and consume either one using the same device.

As used herein, the term "heated aerosol-generating article" refers to an article including an aerosol-forming substrate that is intended to be heated rather than combusted in order to release volatile compounds that can form an aerosol. The heated aerosol-generating article may be an aerosol-generating article for being heated by an electrically operated aerosol-generating device. The aerosol formed by heating the aerosol-forming substrate may contain fewer known harmful constituents than would be produced by combustion or pyrolytic degradation of the aerosol-forming substrate.

As used herein, the term "aerosol-forming substrate" refers to a substrate configured to release volatile compounds that can form an aerosol. An aerosol-forming substrate may be solid or liquid or include both solid and liquid components.

As used herein, the term "liquid aerosol-forming substrate" refers to an aerosol-forming substrate that is in a liquid rather than a solid form. A liquid aerosol-forming substrate may be at least partially absorbed by a liquid retention medium. A liquid-aerosol-forming substrate includes an aerosol-forming substrate in the form of a gel.

As used herein, the term "refillable aerosol-generating article" refers to an article that is configured to be repeatedly filled or loaded with a dose of a liquid aerosol-forming substrate so that the aerosol-forming substrate may be consumed.

As used herein, the term "aerosol-generating device" is a device that engages or interacts with a heated aerosol-generating article to form an inhalable aerosol. The aerosol-generating device may include one or more components used to supply energy from a power supply to heat an aerosol-forming substrate of an aerosol-generating article to generate an aerosol. The aerosol-generating device may be an electrically operated aerosol-generating device including a heating means, or heater, that is operated by electrical power to heat an aerosol-forming substrate of an aerosol-generating article to generate an aerosol. The heating means, or heater, may be a heater for heating air supplied to an aerosol-forming substrate. The heating means, or heater, may be an inductor for heating a susceptor, for example to heat air supplied to an aerosol-forming substrate.

As used herein, the term "outlet end" refers to a portion of the heated aerosol-generating article where aerosol exits the article and is delivered into a user's mouth. In use, a user may draw on the outlet end of the article in order to inhale aerosol generated by the heated aerosol-generating article.

As used herein, the term "distal end" refers to an end of the article that opposes the outlet end.

As used herein, the terms "upstream" and "downstream" are used to describe the relative positions of components, or portions of components, of the heated aerosol-generating article in relation to the direction that air is drawn through the article or system during use. The outlet end of the article may also be referred to as the downstream end and the distal end of the article may also be referred to as the upstream end. Components, or portions of components, of the article may be described as being upstream or downstream of one another based on their relative positions between the mouth or downstream end and the distal or upstream end.

As used herein, the term 'longitudinal' is used to describe the direction between the upstream end and the downstream end of the aerosol-generating article or aerosol-generating device, and the term 'transverse' is used to describe the direction perpendicular to the longitudinal direction.

As used herein, the term 'diameter' is used to describe the maximum dimension in the transverse direction of the aerosol-generating article or aerosol-generating device. As used herein, the term 'length' is used to describe the maximum dimension in the longitudinal direction.

As used herein, the term "liquid retention medium" refers to a component that is configured to releasably retain a liquid aerosol-forming substrate. The liquid retention medium may be, or may include, a porous or fibrous material that absorbs or otherwise retains a liquid aerosol-forming substrate that it is brought into contact with while allowing the liquid aerosol-forming substrate to be released by vaporization.

In some example embodiments, the casing is a rigid casing. For example, the casing may be formed of plastic, metal, or other durable material. The heated aerosol-generating article may be substantially cylindrical in shape. The aerosol-generating article may be substantially elongate. The aerosol-generating article may have a length and a circumference substantially perpendicular to the length. The liquid retention medium may be substantially cylindrical in shape. The liquid retention medium may be substantially elongate. The liquid retention medium may also have a length and a circumference substantially perpendicular to the length.

The aerosol-generating article may have an external diameter of between approximately 5 millimeters and approximately 12 millimeters, for example of between approximately 6 millimeters and approximately 8 millimeters. In an example embodiment, the aerosol-generating article has an external diameter of 7.2 millimeters+/−10 percent.

The aerosol-generating article may have a total length between approximately 25 mm and approximately 100 mm. In one example embodiment, the aerosol-generating article has a total length of approximately 45 mm.

The liquid retention medium may have a length of between about 7 mm and about 20 mm, for example between 8 mm and 15 mm. In one example embodiment, the liquid retention medium may have a length of approximately 10 mm.

The liquid retention medium may have an external diameter that is approximately equal to the external diameter of the aerosol-generating article. The external diameter of the liquid retention medium may be between approximately 5 mm and approximately 12 mm. In one example embodiment, the liquid retention medium may have an external diameter of approximately 7.2 mm+/−10 percent.

A mouthpiece may be located at the outlet end of the article. The mouthpiece may include a filter. The filter may be formed from one or more suitable filtration materials. Many such filtration materials are known in the art. In one example embodiment, the mouthpiece may include a filter formed from cellulose acetate tow.

The mouthpiece may have an external diameter that is approximately equal to the external diameter of the aerosol-generating article. The mouthpiece may have an external diameter of a diameter of between approximately 5 millimeters and approximately 10 millimeters, for example of between approximately 6 millimeters and approximately 8 millimeters. In an example embodiment, the mouthpiece has an external diameter of 7.2 millimeters+/−10%.

The mouthpiece may have a length of between approximately 5 millimeters and approximately 20 millimeters. For example, the mouthpiece may have a length of from about 7 mm to about 12 mm.

The article may include a porous or air-permeable plug located at the distal end of the article. Such a plug may act to help retain the liquid aerosol-forming substrate within the article. The plug may have an external diameter of a diameter of between approximately 5 millimeters and approximately 10 millimeters, for example of between approximately 6 millimeters and approximately 8 millimeters. In an example embodiment, the plug has an external diameter of 7.2 millimeters+/−10%.

The plug may have a length of between approximately 2 millimeters and approximately 10 millimeters. For example, the mouthpiece may have a length of from about 3 mm to about 5 mm.

The liquid retention medium may include an absorbent material, for example an absorbent polymeric material. Examples of suitable liquid retention materials include fibrous polymers and porous polymers such as open-cell foams. The liquid retention medium may include a fibrous cellulose acetate or a fibrous cellulose polymer. The liquid retention medium may include a porous polypropylene material. Suitable materials configured to retain a liquid will be known to the skilled person.

The liquid retention medium is either located within an air-flow path through the heated aerosol-generating article or defines at least a portion of an air-flow path through the aerosol-generating article. In some example embodiments, one or more holes defined through the liquid retention medium define a portion of the air-flow path through the heated aerosol-generating article between the distal end of the article and the outlet end of the article.

The liquid retention medium may be in the form of a tube having a central lumen. Walls of the tube would then be formed from, or include, a suitable liquid-retention material.

In example embodiments, the liquid retention medium is configured to absorb between 105% and 110% of the total volume of a metered dose of the aerosol-forming substrate. This helps to reduce or prevent leakage of liquid aerosol-forming substrate from the article after the liquid aerosol-forming substrate has been loaded. In some example embodiments, the liquid retention medium is between 90% and 95% saturated after being loaded with a dose of the liquid aerosol-forming substrate. In some example embodiments, the liquid retention medium is configured to absorb between 20 and 300 microliters of liquid aerosol-forming substrate, for example between 30 and 200 microliters. Such a range may provide between 10 and 150 puffs of aerosol to a user.

The heated aerosol-generating article includes an aerosol generation section located downstream of the liquid retention medium. In use, the liquid aerosol-forming substrate retained by the liquid retention medium is vaporized and volatile components of the substrate are drawn downstream from the liquid retention medium. The volatile components then cool in the aerosol generation section to form the inhalable aerosol. In some example embodiments, the air with entrained volatile components cools to a temperature of about or below 100° C. within the aerosol generation section. The aerosol generation section may be defined by a space within the article, or by the lumen of a tube within the article. The aerosol generation section may include an aerosol-cooling element, for example an aerosol-cooling element including a gathered sheet of polymeric material. The aerosol-generation section may be at least 2 mm in length, for example between 2 mm and 10 mm in length.

An aerosol-cooling element may have a total surface area of between approximately 300 square millimeters per millimeter length and approximately 1000 square millimeters per millimeter length. In an example embodiment, the aerosol-cooling element has a total surface area of approximately 500 square millimeters per millimeter length.

The aerosol-cooling element may have a low resistance to draw. That is, the aerosol-cooling element may offer a low resistance to the passage of air through the aerosol-generating article. In some example embodiments, the aerosol-cooling element does not substantially affect the resistance to draw of the aerosol-generating article. For example, the aerosol-generation section may include an aerosol-cooling element and have a resistance to draw of lower than 100 mm H2O, for example between 40 and 100 mm H2O.

The aerosol-cooling element may include a plurality of longitudinally extending channels. The plurality of longitudinally extending channels may be defined by a sheet material that has been one or more of crimped, pleated, gathered and folded to form the channels. The plurality of longitudinally extending channels may be defined by a single sheet that has been one or more of crimped, pleated, gathered and folded to form multiple channels. Alternatively, the plurality of longitudinally extending channels may be defined by multiple sheets that have been one or more of crimped, pleated, gathered and folded to form multiple channels.

In some embodiments, the aerosol-cooling element may include a gathered sheet of material selected from metallic foil, polymeric material, and substantially non-porous paper or cardboard. In some embodiments, the aerosol-cooling element may include a gathered sheet of material selected from polyethylene (PE), polypropylene (PP), polyvinylchloride (PVC), polyethylene terephthalate (PET), polylactic acid (PLA), cellulose acetate (CA), and aluminum foil.

In an example embodiment, the aerosol-cooling element includes a gathered sheet of biodegradable material. For example, a gathered sheet of non-porous paper or a gathered sheet of biodegradable polymeric material, such as polylactic acid or a grade of Mater-Bi® (a commercially available family of starch based copolyesters). In an example embodiment, the aerosol-cooling element includes a gathered sheet of polylactic acid.

The aerosol-cooling element may be formed from a gathered sheet of material having a specific surface area of between approximately 10 square millimeters per milligram and approximately 100 square millimeters per milligram weight. In some example embodiments, the aerosol-cooling element may be formed from a gathered sheet of material having a specific surface area of approximately 35 mm2/mg.

The liquid aerosol-forming substrate includes water. In some example embodiments, the liquid aerosol-forming substrate also includes an aerosol-former such as propylene glycol or glycerine. The liquid aerosol-forming substrate may include a flavorant. The liquid aerosol-forming substrate may further include an active ingredient such as nicotine. In some example embodiments, the liquid-aerosol-forming substrate has a water content of between 10 and 25 weight percent, for example between 12 and 20 weight percent. Water is required to form a suitable inhalable aerosol. The liquid aerosol-forming substrate may include a nicotine solution. The liquid aerosol-forming substrate may include a tobacco-containing material including volatile tobacco flavor compounds which are released from the liquid upon heating. The liquid aerosol-forming substrate may include a non-tobacco material. The liquid aerosol-forming substrate may include solvents, ethanol, plant extracts and natural or artificial flavors.

As used herein, the term "aerosol-former" refers to any suitable known compound or mixture of compounds that, in use, facilitates formation of a dense and stable aerosol. An aerosol-former is substantially resistant to thermal degradation at the operating temperature of the aerosol-generating article. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Example aerosol formers are polyhydric alcohols or mixtures thereof, such as triethylene glycol, 1,3-butanediol and glycerine.

A heated aerosol-generating system may be provided including an aerosol-generating device and a heated aerosol-generating article according to any of the example embodiments discussed above. In some example embodiments, the aerosol-generating device is an electrically operated aerosol-generating device.

An aerosol-generating device may be described as a heated aerosol-generating device, which is an aerosol-generating device including a heating element or heater. The heating element or heater is used to heat an aerosol-forming substrate of an aerosol-generating article to generate an aerosol.

An aerosol-generating device may be an electrically heated aerosol-generating device, which is an aerosol-generating device including a heating element that is operated by electrical power to heat an aerosol-forming substrate of an aerosol-generating article to generate an aerosol.

The aerosol-generating device of the aerosol-generating system may include a housing having a cavity for receiving the heated aerosol-generating article and a controller configured to control the supply of power from a power supply to an electric heating element of the system.

The electric heating element may include one or more heating elements.

In some example embodiments, the electrically operated aerosol-generating device includes an electric heating element and a housing having a cavity, and wherein the heated aerosol-generating article is received in the cavity. The heating element may conveniently be shaped as a needle, pin, rod, or blade that may be inserted into the article.

Aerosol-generating systems according to the example embodiments may include an electric heating element. The electric heating element may include one or more external heating elements, one or more internal heating elements, or one or more external heating elements and one or more internal heating elements.

The one or more external heating elements may include an array of external heating elements arranged around the inner surface of the cavity. In certain examples, the external heating elements extend along the longitudinal direction of the cavity. With this arrangement, the heating elements may extend along the same direction in which the article is inserted into and removed from the cavity. This may reduce interference between the heating elements and the article relative to devices in which the heating elements are not aligned with the length of the cavity. In some embodiments, the external heating elements extend along the length direction of the cavity and are spaced apart in the circumferential direction. Where the heating element includes one or more internal heating elements, the one or more internal heating elements may include any suitable number of heating elements. For example, the heating element may include a single internal heating element. The single internal heating element may extend along the longitudinal direction of the cavity.

The electric heating element may include an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may include doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminum- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and iron-manganese-aluminum based alloys. Timetal® is a registered trade mark of Titanium Metals Corporation, 1999 Broadway Suite 4300, Denver Colorado In composite materials, the electrically resistive material may optionally be embedded in, encapsulated or coated with an insulating material or vice-versa, depending on the kinetics of energy transfer and the external physicochemical properties required. The heating element may include a metallic etched foil insulated between two layers of an inert material. In that case, the inert material may include Kapton®, all-polyimide or mica foil. Kapton® is a registered trade mark of E.I. du Pont de Nemours and Company, 1007 Market Street, Wilmington, Delaware 19898, United States of America.

Where the electric heating element includes a susceptor, the aerosol-generating device may include an inductor arranged to generate a fluctuating electromagnetic field within the cavity and an electrical power supply connected to the inductor. The inductor may include one or more coils that generate a fluctuating electromagnetic field. The coil or coils may surround the cavity.

In some example embodiments, the device is configured to generate a fluctuating electromagnetic field of between 1 and 30 MHz, for example, between 2 and 10 MHz, for example between 5 and 7 MHz. In some example embodiments, the device is configured to generate a fluctuating electromagnetic field having a field strength (H-field) of between 1 and 5 kA/m, for example between 2 and 3 kA/m, for example about 2.5 kA/m.

In an example heated aerosol-generating system, an airflow path is defined when the refillable aerosol-generating article is coupled to the aerosol-generating device. The air flow path include a point at which air enters the aerosol-generating device, a point at which air passes into the heated aerosol-generating article, a point at which air passes over the liquid retention medium, and a point at which air passes out of the outlet end of the heated aerosol-generating article and into a user's mouth. In an example system, the aerosol-generating device acts to heat air at a point between entry into the aerosol-generating device and passing over the liquid retention medium. This allows heated air to vaporize a liquid aerosol-forming substrate retained by the liquid retention medium. Heating of the air may be accomplished by a heater such as a heating coil that is located within the airflow path and acts to directly heat the air prior to that air passing over the liquid retention medium.

The heated aerosol-generating system may include an air permeable heat accumulator or heat diffuser that is arranged in the air flow path to heat air. The term heat diffuser is used below. The heat diffuser may interact with a heater and take on heat energy. The heat energy is then passed to air passing through the heat diffuser. A heat diffuser may be a component having a high surface area and high porosity. Air should be able to flow through the heat diffuser without undergoing a significant pressure drop. Examples of suitable heat diffusers may be a porous metallic foam or a porous ceramic foam component arranged both in thermal contact with a heater and within the air flow path of the heated aerosol-generating system.

The refillable aerosol-generating article may include a heat diffuser located upstream of the liquid retention section, the heat diffuser being configured to heat air drawn into the article when the article is coupled to an electrically-operated aerosol-generating device. In some example embodiments, the heat diffuser is configured to engage with or thermally interact with heating elements of a separate aerosol-generating device. The heat diffuser may be heated by the aerosol-generating device and heat air that passes through the heat diffuser prior to passing through the liquid retention section. The heated air then acts to volatilize the liquid aerosol-forming substrate.

A heat diffuser may be a removable component of a heated aerosol-generating system. For example, heat diffuser may be in the form of a removably couplable component that engages with an aerosol generating device to alter the manner in which the aerosol generating device heats aerosol generating articles. As an example, an aerosol generating device may include an insertable heating element for insertion into a solid aerosol forming substrate of a heated aerosol-generating article. The heating element contacts the solid aerosol-forming substrate and heats it to generate an aerosol. A heat diffuser may be configured to engage with the insertable heating element. The heat diffuser may then be heated by the heating element and heat air that passes through the heating element. The heated air may then volatilize an aerosol-forming substrate of a heated aerosol-generating article that is located downstream of the heat diffuser. In this way the manner in which the aerosol-generating device heats an aerosol-forming substrate may be changed from direct contact to indirect heating of air. The same aerosol-generating device may then be used to heat different types of aerosol-generating article, thereby providing a greater choice to the user.

An example system may include a heated aerosol-generating device, at least one aerosol-generating article as described above, a source of liquid aerosol-forming substrate, and at least one heated aerosol-forming article having a solid aerosol-forming substrate, for example an aerosol-forming substrate made from homogenized tobacco material. If the article does not include a heat diffuser, the system may further include a removably couplable heat diffuser for engagement with the aerosol-generating device to change the manner in which the aerosol-generating device provides heat to the aerosol-forming substrate.

In some example embodiments, the aerosol-generating device is a portable or handheld aerosol-generating device that is comfortable for a user to hold between the fingers of a single hand.

The aerosol-generating device may be substantially cylindrical in shape

The aerosol-generating device may have a length of between approximately 70 millimeters and approximately 120 millimeters.

The device may include a power supply for supplying electrical power to the electric heating element. The power supply may be any suitable power supply, for example a DC voltage source such as a battery. In one example embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The controller may be a simple switch. Alternatively the controller may be electric circuitry and may include one or more microprocessors or microcontrollers.

An aerosol-generating kit may be provided including a refillable heated aerosol-generating article according to any embodiment or configuration described above and a dispenser of aerosol-forming liquid. The dispenser is configured to dispense a metered dose of the aerosol-forming liquid through the opening or port of the refillable heated aerosol-generating article to charge the liquid retention section. In some example embodiments, the metered dose is between 75% and 95% of the volume of liquid required to fully saturate the liquid retention medium.

The aerosol-forming liquid of the kit may include between 10 weight percent and 25 weight percent water, an aerosol former, and at least one flavorant.

Figure 1:
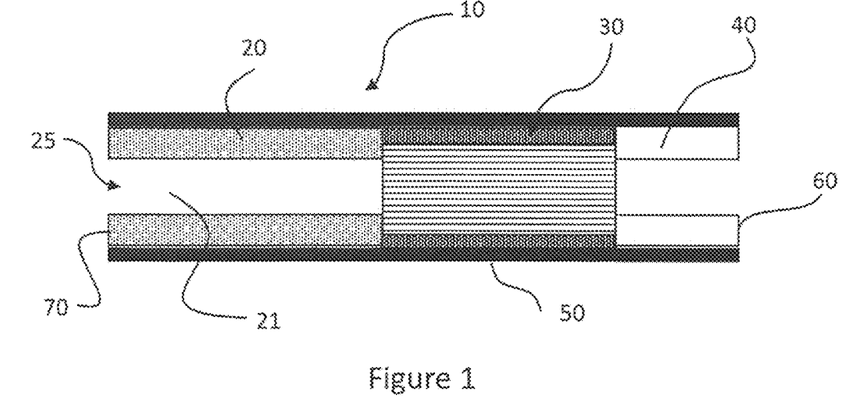
FIG. 1 shows a refillable aerosol-generating article according to a first example embodiment.

FIG. 1 illustrates a refillable aerosol-generating article 10 according to a first example embodiment. The refillable aerosol-generating article includes a tubular liquid retention medium 20, a cylindrical aerosol-generation section 30, and a mouthpiece 40. These three components are arranged co-axially and contained within a rigid tubular casing 50. The refillable aerosol-generating article is in the form of a substantially cylindrical rod and has an outlet end 60 and a distal end 70 opposite to the outlet end. The tubular liquid retention medium has a lumen 21. The lumen 21 defines an opening 25 at the distal end 70 of the article which provides access to the liquid retention medium. The liquid retention medium may be filled with a liquid aerosol-forming substrate through the opening. The total length of the article 10 is 45 mm and it has an outer diameter of 7.2 mm.

The tubular liquid retention medium 20 has a length of 20 mm and is formed from fibrous cellulose acetate material. The liquid retention medium has a capacity to absorb 35 microliters of liquid. The lumen 21 of the tubular liquid retention medium provides an air flow path through the liquid retention medium. The material of the liquid retention medium may be any other suitable fibrous or porous material.

A suitable liquid aerosol-forming substrate (not shown) includes propylene glycol, nicotine extract, and 20 weight percent water. A wide range of flavorants may be optionally added. A wide range of aerosol-formers may be used as alternative, or in addition to, propylene glycol. In some example embodiments, the liquid aerosol-forming substrate is contained within a metered dispenser. For the example embodiment, a volume of between 30 and 33 microliters may be dispensed to load the liquid retention material to between 90 and 95% saturation. This may be sufficient for between 15-16 puffs.

The aerosol-generating section 30 has a length of 18 mm and includes a crimped and gathered sheet of polymeric material. The sheet of polymeric material is not densely packed and the aerosol-generating section does not cause significant pressure drop in air passing through the section.

The crimped and gathered sheet of polymeric material may be termed an aerosol-cooling element and has a length of about 18 mm, an outer diameter of about 7.12 mm, and an inner diameter of about 6.9 mm. In one example embodiment, the aerosol-cooling element is formed from a sheet of polylactic acid having a thickness of 50 mm±2 mm. The sheet of polylactic acid has been crimped and gathered to define a plurality of channels that extend along the length of the aerosol-cooling element. The total surface area of the aerosol-cooling element is between 8000 mm2 and 9000 mm2, which is equivalent to approximately 500 mm2 per mm length of the aerosol-cooling element. The specific surface area of the aerosol-cooling element is approximately 2.5 mm2/mg and it has a porosity of between 60% and 90% in the longitudinal direction. The polylactic acid is kept at a temperature of 160 degrees Celsius or less during use.

Porosity is defined herein as a measure of unfilled space in a rod including material such as an aerosol-cooling element. For example, if a diameter of the rod was 50% unfilled by the aerosol-cooling element, the porosity would be 50%. Likewise, a rod would have a porosity of 100% if the inner diameter was completely unfilled and a porosity of 0% if completely filled. The porosity may be calculated using known methods.

The mouthpiece is a rigid hollow tube formed from cellulose acetate and has a length of 7 mm.

The casing 50 is formed from polypropylene. Many other suitable polymers or materials such as metals are known. The casing locates the other components of the article in position and is resilient enough for repeated use.

Figure 2:
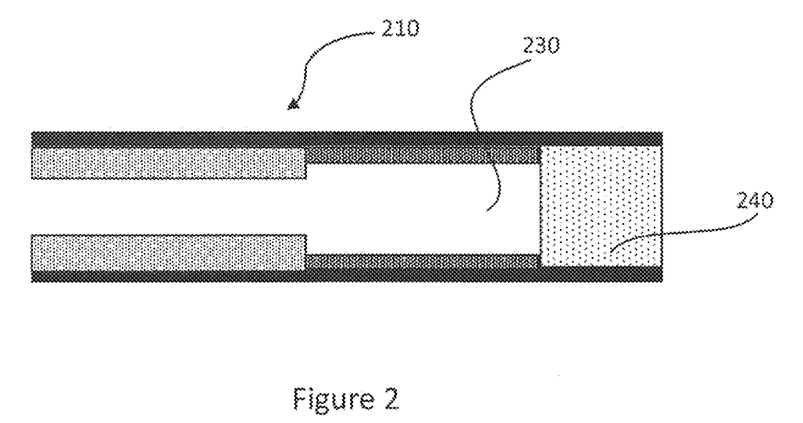
FIG. 2 shows a refillable aerosol-generating article according to a second example embodiment.
Figure 3:
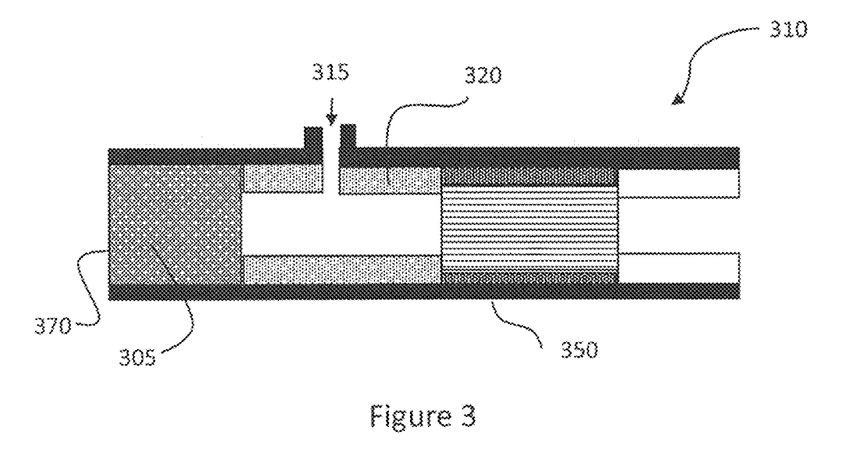
FIG. 3 shows a refillable aerosol-generating article according to a third example embodiment.

FIGS. 2 and 3 illustrate alternative embodiments of refillable aerosol-generating articles according to example embodiments.

FIG. 2 illustrates a refillable aerosol-generating article 210 that is identical to the article 10 described above in relation to FIG. 1 with the exceptions that the aerosol-generation section 230 is a hollow tube, without an aerosol-cooling element, and the mouthpiece 240 is a filter formed from cellulose acetate tow. Other suitable filters such as mouthpiece filters are known in the art.

FIG. 3 illustrates a refillable aerosol-generating article 310, according to some example embodiments, that is identical to the article 10 described in relation to FIG. 1 with the additional features that the article includes a heat diffuser 305 and in that a port 315 is defined through a side-wall of the casing 350.

The heat diffuser 305 is a substantially cylindrical element formed from glass fibre. The heat diffuser 305 may be made from other porous materials such as ceramic fibres, ceramic foams, or sintered metals. The heat diffuser defines one or more longitudinally extending slots that allow the heat diffuser element to be penetrated by a heating element of an aerosol-generating device. The heat diffuser may be configured to accumulate heat from a heater and then use this accumulated heat to heat air passing through the heat diffuser.

The heat diffuser 305 spans the distal end 370 of the article 410. The front plug is formed of a highly porous cellulose acetate material and provides an air flow path into the article 310. The heat diffuser may additionally help to reduce or prevent egress of liquid aerosol-forming substrate during use of the article.

The port 315 includes an opening defined through a side wall of the casing 350 and provides access to the liquid retention medium 320. The liquid retention medium may be filled with a liquid aerosol-forming substrate through the port 315.

Methods of using a heated aerosol-generating article according to example embodiments will be described with relation to the articles of FIGS. 1 and 3.

Aerosol-generating devices for heating heated aerosol-generating articles having a solid aerosol-forming substrate are known in the art. In all embodiments described below, the first step is to fill or charge the article with a dose of liquid aerosol-forming substrate from a suitable dispenser. The dose of liquid-forming substrate is injected or otherwise introduced to the liquid retention material through a suitable opening 25 or port 315. The article 10, 310 is thus primed and ready for engagement with an aerosol-generating device.

Figure 4:
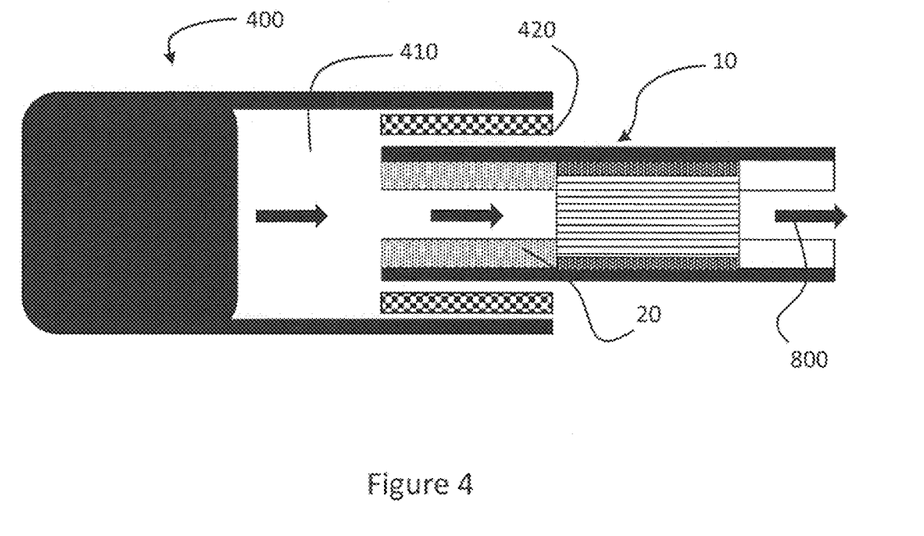
FIG. 4 shows a heated aerosol-generating article according to the first example embodiment, during use, engaged with an aerosol-generating device having external heating elements.

FIG. 4 illustrates the use of an aerosol-generating device having external heating elements, according to some example embodiments. Such an aerosol-generating device is known in the art for the consumption of aerosol-generating articles having solid aerosol-forming substrates. The device 400 defines a cavity 410 for receiving a distal portion of the refillable aerosol-generating article 10. A plurality of external heating elements 420 are located in the cavity and, when the article 10 is engaged within the cavity 410 the heating elements 420 surround the liquid retention medium 20. The external heating elements may be activated and then heat the liquid retention medium through the casing 50 by conduction and/or radiation. The liquid aerosol-forming substrate retained within the liquid retention section is heated and volatilised. As a user draws on the outlet end 60 of the article 10 the volatilised aerosol-forming substrate is entrained in the air drawn into the aerosol-generation section 30 of the article 10. The volatilised aerosol-forming substrate cools within the aerosol-cooling section and condenses to form an inhalable aerosol. The inhalable aerosol is then inhaled by the user. The air flow path is shown by the arrows 800.

Figure 5:
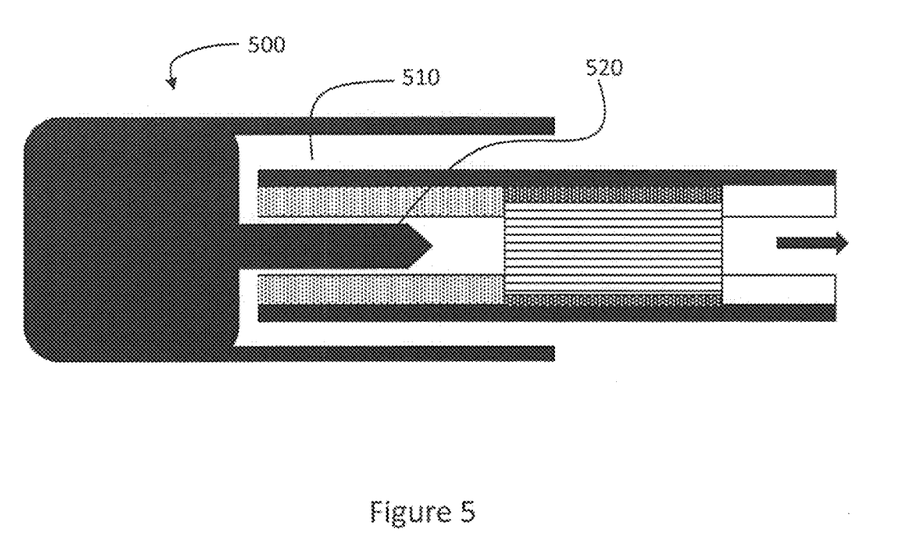
FIG. 5 shows a heated aerosol-generating article according to the first example embodiment, during use, engaged with an aerosol-generating device having an internal heating element.

FIG. 5 illustrates the use of an aerosol-generating device having an internal heating element, according to some example embodiments. Such an aerosol-generating device is known in the art for the consumption of aerosol-generating articles having solid aerosol-forming substrates. The device 500 defines a cavity 510 for receiving a distal portion of the refillable aerosol-generating article 10. A blade shaped heating element 520 is located in the cavity and, when the article 10 is engaged within the cavity 510 the heating element 520 extends into the lumen of the liquid retention medium. The internal heating element may be activated and then heat the liquid retention medium by radiation. The liquid aerosol-forming substrate retained within the liquid retention section is heated and volatilised. As a user draws on the outlet end 60 of the article 10 the volatilised aerosol-forming substrate is entrained in the air drawn into the aerosol-generation section 30 of the article 10. The volatilised aerosol-forming substrate cools within the aerosol-cooling section and condenses to form an inhalable aerosol. The inhalable aerosol is then inhaled by the user.

Figure 6:
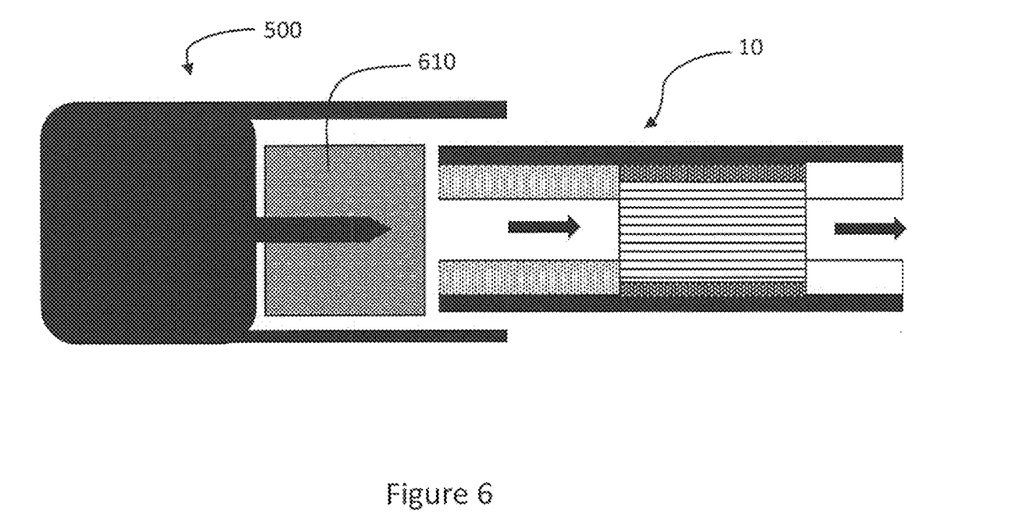
FIG. 6 shows a heated aerosol-generating article according to the first example embodiment, during use, engaged with an aerosol-generating device having an internal heating element and a removably-couplable heat diffuser.

FIG. 6 illustrates an example method of using the refillable aerosol-generating article 10. The aerosol-generating device is an aerosol-generating device having an internal heating element as described in relation to FIG. 5. The aerosol-generating device 500 is engaged with a heat diffuser element 610 as well as the refillable aerosol-generating article 10. The heat diffuser element 610 is a substantially cylindrical element formed from glass fibre. The heat diffuser element may be made from other porous materials such as ceramic fibres, ceramic foams, or sintered metals. The heat diffuser element defines one or more longitudinally extending slots that allow the heat diffuser element to be penetrated by the heating element 520 of the aerosol-generating device 500. The internal heating element may be activated and then heat the heat diffuser element 610 by conduction and/or radiation. As a user draws air through the system, the air passes through the heated heat diffuser 610 and is heated up. This heated air is then drawn into the aerosol-generating article and passes through the liquid retention medium. The liquid aerosol-forming substrate retained within the liquid retention section is heated by this heated air and volatilised. As a user continues to draw on the outlet end 60 of the article 10, the volatilised aerosol-forming substrate is entrained in the air drawn into the aerosol-generation section 30 of the article 10. The volatilised aerosol-forming substrate cools within the aerosol-cooling section and condenses to form an inhalable aerosol. The inhalable aerosol is then inhaled by the user.

Figure 7:
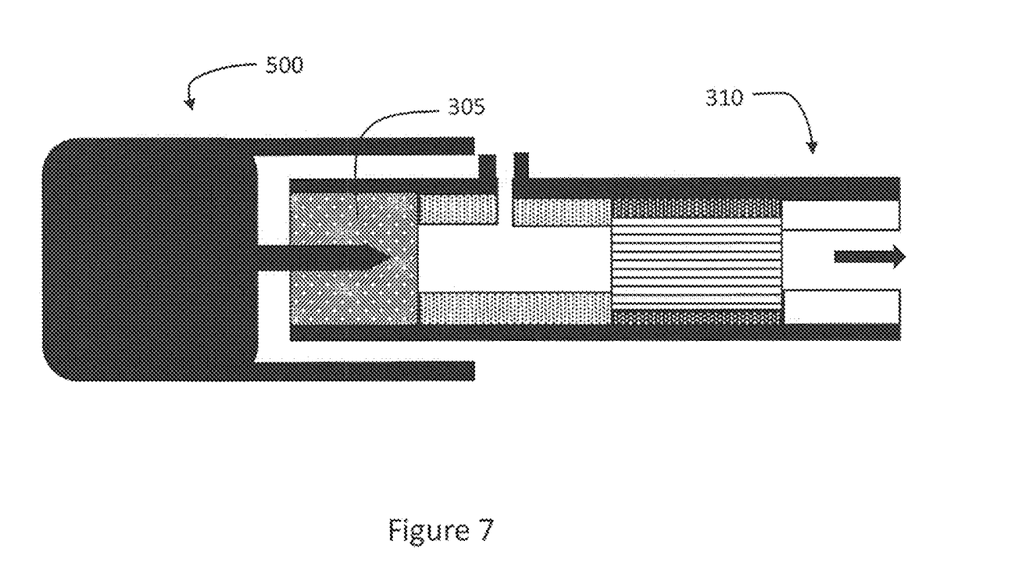
FIG. 7 shows a heated aerosol-generating article according to the third example embodiment, during use, engaged with an aerosol-generating device having an internal heating element.

FIG. 7 illustrates an example method of using a refillable aerosol-generating article 310 according to the third embodiment, and described above in relation to FIG. 3. The refillable aerosol-generating article 310 includes an integral heat diffuser. Thus, the article 310 can interact with an aerosol-generating device 500 directly. The heat diffuser 305 defines one or more longitudinally extending slots that allow the heat diffuser to be penetrated by the heating element 520 of the aerosol-generating device 500. The internal heating element may be activated and then heat the heat diffuser 305 by conduction and/or radiation. As a user draws air through the system, the air passes into the article 310 and through the heated heat diffuser 305, and is heated up. This heated air is then drawn through the liquid retention medium. The liquid aerosol-forming substrate retained within the liquid retention section is heated by this heated air and volatilised. As a user continues to draw on the outlet end of the article 310, the volatilised aerosol-forming substrate is entrained in the air drawn into the aerosol-generation section of the article 310. The volatilised aerosol-forming substrate cools within the aerosol-cooling section and condenses to form an inhalable aerosol. The inhalable aerosol is then inhaled by the user.

The invention claimed is:

1. An aerosol-generating device comprising:
   a refillable liquid retention section within a casing;
   a heat diffuser located upstream of the refillable liquid retention section, the heat diffuser defining at least one longitudinally extending slot;
   a heating element configured to heat liquid of the refillable liquid retention section, the heating element penetrating the at least one longitudinally extending slot of the heat diffuser, the heating element entirely upstream of the refillable liquid retention section; and
   an aerosol-generation section within the casing.

2. The aerosol-generating device of claim 1, wherein the heating element is configured to indirectly heat the refillable liquid retention section by radiation.

3. The aerosol-generating device of claim 1, wherein the refillable liquid retention section includes a liquid retention medium having a capacity.

4. The aerosol-generating device of claim 3, wherein the liquid retention medium is an absorbent material defining at least one channel through which air can pass.

5. The aerosol-generating device of claim 3, wherein the liquid retention medium comprises an absorbent polymeric material.

6. The aerosol-generating device of claim 1, wherein the aerosol-generation section is located downstream of the refillable liquid retention section.

7. The aerosol-generating device of claim 1, further comprising:
   an outlet end and a distal end upstream from the outlet end and is configured such that air can be drawn therethrough from the distal end to the outlet end, passing through the refillable liquid retention section.

8. The aerosol-generating device of claim 1, further comprising:
   an opening or port for allowing the refillable liquid retention section to be filled with liquid.

9. The aerosol-generating device of claim 8, wherein the opening or port is defined through the casing at a point between a distal end and an outlet end.

10. The aerosol-generating device of claim 1, wherein the casing is a rigid casing.

11. The aerosol-generating device of claim 1, wherein the aerosol-generation section is an empty chamber of at least 2 mm in length.

12. The aerosol-generating device of claim 1, wherein the aerosol-generation section comprises an aerosol-cooling element and has a resistance to draw that is lower than 100 mm H2O.

13. An aerosol-generating device comprising:
    a refillable liquid retention section within a casing;
    an aerosol-generation section within the casing;
    a heat diffuser located upstream of the refillable liquid retention section, the heat diffuser defining at least one longitudinally extending slot;
    a heating element configured to heat liquid of the refillable liquid retention section, the heating element penetrating the at least one longitudinally extending slot of the heat diffuser, the heating element entirely upstream of the refillable liquid retention section; and
    a filter at an outlet end of the aerosol-generating device, the filter being downstream from the aerosol-generation section.

14. The aerosol-generating device of claim 13, wherein the heat diffuser is configured to indirectly heat air drawn into the aerosol-generating device.

15. An aerosol-generating kit comprising:
    a refillable heated aerosol-generating article for use with an electrically-operated aerosol-generating device, the refillable heated aerosol-generating article including,
    a refillable liquid retention section within a casing,
    a heat diffuser located upstream of the refillable liquid retention section, the heat diffuser defining at least one longitudinally extending slot,
    a heating element configured to heat liquid of the refillable liquid retention section, the heating element penetrating the at least one longitudinally extending slot of the heat diffuser, the heating element entirely upstream of the refillable liquid retention section, and
    an aerosol-generation section within the casing.

16. The aerosol-generating kit of claim 15, further comprising:
    a dispenser of aerosol-forming liquid, the dispenser being configured to dispense a metered dose of the aerosol-forming liquid through an opening or port of the refillable heated aerosol-generating article to charge the refillable liquid retention section.

17. The aerosol-generating kit of claim 16, wherein the aerosol-forming liquid comprises between 10 weight percent and 25 weight percent water, an aerosol former, and at least one flavorant.

18. The aerosol-generating kit of claim 16, wherein the metered dose is between 75% and 95% of a liquid volume required to fully saturate a liquid retention medium of the refillable liquid retention section.

19. The aerosol-generating kit of claim 15, wherein the refillable heated aerosol-generating article includes an outlet end and a distal end upstream from the outlet end.

20. The aerosol-generating kit of claim 15, wherein the heating element includes an inductor configured to heat a susceptor to heat air drawn into the refillable heated aerosol-generating article.

* * * * *